United States Patent
Pérez et al.

(10) Patent No.: US 11,795,153 B1
(45) Date of Patent: Oct. 24, 2023

(54) EPOXIDE COMPOUNDS, METHODS OF PREPARATIONS AND USES THEREOF

(71) Applicant: Zschimmer & Schwarz, Inc., Milledgeville, GA (US)

(72) Inventors: Antonio Leyva Pérez, Valencia (ES); Judit Oliver Meseguer, Valencia (ES); Susi Hervàs Arnandis, Valencia (ES); Douglas G. Placek, Yardley, PA (US)

(73) Assignee: ZSCHIMMER & SCHWARZ, INC., Milledgeville, GA (US)

( * ) Notice: Subject to any disclaimer, the term of this patent is extended or adjusted under 35 U.S.C. 154(b) by 0 days.

(21) Appl. No.: 17/805,372

(22) Filed: Jun. 3, 2022

(51) Int. Cl.
| | | |
|---|---|---|
| *C07D 301/12* | (2006.01) | |
| *B01J 21/04* | (2006.01) | |
| *B01J 35/02* | (2006.01) | |
| *C10M 105/18* | (2006.01) | |
| *B01J 35/08* | (2006.01) | |
| *C10N 70/00* | (2006.01) | |

(52) U.S. Cl.
CPC ............ *C07D 301/12* (2013.01); *B01J 21/04* (2013.01); *B01J 35/026* (2013.01); *B01J 35/08* (2013.01); *C10M 105/18* (2013.01); *C10M 2207/042* (2013.01); *C10N 2070/00* (2013.01)

(58) Field of Classification Search
CPC ....... C07D 301/12; B01J 21/04; B01J 35/026; B01J 35/08; C10M 105/18; C10M 2207/042; C10N 2070/00
USPC ......................................................... 549/531
See application file for complete search history.

(56) References Cited

U.S. PATENT DOCUMENTS

| | | | |
|---|---|---|---|
| 7,544,645 B2 | 6/2009 | Miller et al. | |
| 7,867,959 B2 | 1/2011 | Miller et al. | |
| 7,871,967 B2 | 1/2011 | Miller et al. | |
| 8,304,574 B2 | 11/2012 | Elomari et al. | |
| 8,324,423 B2 | 12/2012 | Miller et al. | |
| 8,410,033 B2 | 4/2013 | Zhou et al. | |
| 8,481,465 B2 | 7/2013 | Elomari et al. | |
| 8,507,423 B2 | 8/2013 | Elomari et al. | |
| 8,575,081 B2 | 11/2013 | Miller et al. | |
| 8,586,519 B2 | 11/2013 | Miller et al. | |
| 2006/0014970 A1* | 1/2006 | Goebbel | B01J 19/2465 |
| | | | 549/529 |
| 2014/0228263 A1 | 8/2014 | Okazaki et al. | |

FOREIGN PATENT DOCUMENTS

| | | | |
|---|---|---|---|
| CN | 103687935 A | 3/2014 | |
| WO | WO 2011/146426 | * | 11/2011 |
| WO | WO 2014/078691 A1 | * | 5/2014 |

OTHER PUBLICATIONS

Anelli, P.L., et al., "Synergistic effect of lipophilic carboxylic acids and heterocyclic axial ligands in alkene epoxidation by hydrogen peroxide catalysed by manganese(III) tetra-aryl porphyrins", Chem. Commun., 1989, pp. 779-780.
Brandolin, S.E., et al., "UNIFAC Evaluation of the Liquid-Liquid Phase Equilibrium during Lipase-Catalyzed Peracidation of Different Carboxylic Acids", J. of Chem. & Eng. Data, 2022, vol. 67, No. 8, pp. 1994-2003.
Buffon, R., et al., "Heterogenization of alkene epoxidation catalysts", J. Braz. Chem. Soc., vol. 14, No. 3, 2003, pp. 347-353.
Camblor, M.A., et al., "Epoxidation of unsaturated fatty esters over large-pore Ti-containing molecular sieves as catalysts: important role of the hydrophobic-hydrophilic properties of the molecular sieve", Chem. Commun., 1997, pp. 795-796.
Cesquini, R.G., et al., "Alumina-Catalyzed Epoxidation with Hydrogen Peroxide: Recycling Experiments and Activity of Sol-Gel Alumina", Adv. Synth. Catal., vol. 344, Issue 8, Sep. 2002, pp. 911-914.
Corma, A., et al., "Oxidation of Olefins with Hydrogen Peroxide and tert-Butyl Hydroperoxide on Ti-Beta Catalyst", J. Catal., vol. 152, 1995, pp. 18-24.
De Vos, D., et al., "Highly selective epoxidation of alkenes and styrenes with H2O2 and manganese complexes of the cyclic triamine 1,4,7-trimethyl-1,4,7-triazacyclononane", Chem. Commun., 1996, pp. 917-918.
De Vos, D.E., et al., "Epoxidation of terminal or electron-deficient olefins with H2O2, catalysed by Mn-trimethyltriazacyclonane complexes in the presence of an oxalate buffer", Tetrahedron Lett., vol. 39, 1998, pp. 3221-3224.
Fraile, J.M. et al., "Epoxidation of electron-deficient alkenes using heterogeneous basic catalysts" Stud. Surf. Sci. Catal.,vol. 130, 2000, pp. 1673-1678.
Gordon, C.P., et al., "Efficient epoxidation over dinuclear sites in titanium silicalite-1", Nature, vol. 586, 2020, pp. 708-713.
Grigoropoulou, G., et al., "Recent developments on the epoxidation of alkenes using hydrogen peroxide as an oxidant", Centre for Clean Technology, vol. 5, 2003, pp. 1-7.
Ishii, Y., et al., "Hydrogen peroxide oxidation catalyzed by heteropoly acids combined with cetylpyridinium chloride. Epoxidation of olefins and allylic alcohols, ketonization of alcohols and diols, and oxidative cleavage of 1,2-diols and olefins", J. Org. Chem., vol. 53, No. 15, 1988, pp. 3587-3593.

(Continued)

*Primary Examiner* — Taylor V Oh
(74) *Attorney, Agent, or Firm* — Smith, Gambrell & Russell; Judy Jarecki-Black; Ram W. Sabnis

(57) ABSTRACT

Processes for preparing epoxide compounds are provided. Processes for using epoxide compounds and their industrial applications are also provided.

20 Claims, No Drawings

(56) References Cited

OTHER PUBLICATIONS

Kazuhiko, S. et al., "A Halide-Free Method for Olefin Epoxidation with 30% Hydrogen Peroxide", Bull. Chem. Soc. Jpn., vol. 70, No. 4, 1997, pp. 905-915.

Khalfallah-Boudali, L., et al., "Characterization and catalytic properties of titanium pillared clays in the epoxidation of allylic alcohols", Stud. Surf. Sci. Catal., vol. 130, 2000, pp. 1643-1648.

Klein, J.E., "Epoxidation of Alkenes by Peracids: From Textbook Mechanisms to a Quantum Mechanically Derived Curly-Arrow Depiction", ChemistryOpen, vol. 8, No. 10, Jul. 12, 2019, pp. 1244-1250.

Leffler, J.E., et al., "Reaction of diacyl peroxides with alumina", Amer. Chem. Soc., vol. 99, No. 2, 1977, pp. 480-483.

Lueangchaichaweng, W., et al., "High surface area, nanostructured boehmite and alumina catalysts: Synthesis and application in the sustainable epoxidation of alkenes", Appl. Catal. A: General, vol. 571, 2019, pp. 180-187.

Mandelli, D., et al., "Alumina-catalyzed alkene epoxidation with hydrogen peroxide", Appl. Catal. A: Gen., vol. 219, Issue 1-2, Oct. 5, 2001, pp. 209-213.

Mas-Ballesté, R., et al., "Iron-Catalyzed Olefin Epoxidation in the Presence of Acetic Acid:? Insights into the Nature of the Metal-Based Oxidant", J. Am. Chem. Soc., vol. 129, 2007, pp. 15964-15972.

Nishiyama, Y., et al., "High Turnover Numbers for the Catalytic Selective Epoxidation of Alkenes with 1 atm of Molecular Oxygen", Angew. Chem. Int. Ed., vol. 40, 2001, pp. 3639-3641.

Rebek, J., et al., "New epoxidation reagents derived from alumina and silicon", Tetrahedron Lett., vol. 20, 1979, pp. 4337-4338.

Rudolph, J., et al., "Highly Efficient Epoxidation of Olefins Using Aqueous H2O2 and Catalytic Methyltrioxorhenium/Pyridine:? Pyridine-Mediated Ligand Acceleration", J. Am. Chem. Soc., vol. 119, 1997, pp. 6189-6190.

Ruesch gen, M., et al., "Chemoenzymatic Epoxidation of Alkenes by Dimethyl Carbonate and Hydrogen Peroxide", Org. Lett., vol. 1, No. 7, 1999, pp. 1025-1026.

Sales, H. J., et al., "Epoxidation of soybean oil catalysed by CH3ReO3/H2O2", Stud. Surf. Sci. Catal., vol. 130, 2000, pp. 1661-1666.

Sepulveda, J., et al., "Alumina-catalyzed epoxidation of unsaturated fatty esters with hydrogen peroxide", Appl. Catal. A: General, vol. 318, 2007, pp. 213-217.

Shu, L., et al., "An Efficient Ketone-Catalyzed Epoxidation Using Hydrogen Peroxide as Oxidant", J. Org. Chem., vol. 65, 2000, pp. 8807-8810.

Van Vliet, M.C.A., et al., "Alumina: a cheap, active and selective catalyst for epoxidations with (aqueous) hydrogen peroxide", Green Chem., vol. 3, No. 5, Oct. 2001, pp. 243-246.

Van Vliet, M.C.A., et al., "Methyltrioxorhenium-catalysed epoxidation of alkenes in trifluoroethanol", Chem. Commun., Issue 9, 1999, pp. 821-822.

Venturello, C., et al., "A new, effective catalytic system for epoxidation of olefins by hydrogen peroxide under phase-transfer conditions", J. Org. Chem., vol. 48, No. 21, 1983, pp. 3831-3833.

Venturello, C., et al., "Quaternary ammonium tetrakis(diperoxotungsto)phosphates(3-) as a new class of catalysts for efficient alkene epoxidation with hydrogen peroxide", J. Org. Chem., vol. 53, No. 7, 1988, pp. 1553-1557.

Wang, J.A., et al., "Aluminum Local Environment and Defects in the Crystalline Structure of Sol-Gel Alumina Catalyst", Phys. Chem. B, vol. 103, 1999, pp. 299-303.

Wilde, N., et al., "Accessibility enhancement of TS-1-based catalysts for improving the epoxidation of plant oil-derived substrates", Catal. Sci. Technol., vol. 6, 2016, pp. 7280-7288.

Wilde, N., et al., "Epoxidation of biodiesel with hydrogen peroxide over Ti-containingsilicate catalysts", Micropor. Mesopor. Mater., vol. 164, 2012, pp. 182-189.

Yang, Q., et al., "Epoxidation of olefins on M-SiO2 (M=Ti, Fe, V) catalysts with highly isolated transition metal ions prepared by ion beam implantation", Stud. Surf. Sci. Catal., vol. 130, 2000, pp. 221-226.

* cited by examiner

EPOXIDE COMPOUNDS, METHODS OF PREPARATIONS AND USES THEREOF

FIELD OF THE INVENTION

Embodiments described herein generally relate to epoxide compounds. More particularly, such embodiments relate to methods of making and using epoxide compounds and industrial applications thereof.

BACKGROUND OF THE INVENTION

Epoxides are key raw materials for a wide variety of products (Franz, G.; Sheldon, R. A. in: Elvers, B.; Hawkins, S.; Shulz G. (Eds.), *Ullmann's Encyclopedia of Industrial Chemistry, Vol. A* (18), 5th Edition, VCH, Weinheim, 1991, 261-311; Lutz, J. T. in: Grayson, M.; Eckroth, D.; Bushey, G. J.; Eastman, C. I.; Klingsberg, A.; Spiro L. (Eds.), *Kirk-Othmer Encyclopedia of Chemical Technology, Vol. 9*, 3rd Edition, Wiley, New York, 1980, 251) and much effort is devoted to the development of new active and selective epoxidation catalysts for processes that increase the rate of conversion and selectivity, avoiding the formation of significant amounts of by-products. For alkenes with more than two carbon atoms, liquid-phase epoxidation with peracids is still the most widely used method, in spite of being a slow reaction and producing large amounts of carboxylic acid by-products. An alternative to avoid the formation of such carboxylic acid by-products is the use of hydrogen peroxide as an oxidizing agent in the presence of a catalyst, which gives a clean and environmentally friendly reaction, since the starting material is relatively safe and inexpensive, and only water is formed as a by-product (Strukul G. in Strukul, G. (Ed.), *Catalytic Oxidation with Hydrogen Peroxide as Oxidant*, Kluwer Academic Publishers, Dordrecht, 1992, 6). Epoxidation with $H_2O_2$ alone is not effective. The described catalysts to perform the epoxidation in the presence of hydrogen peroxide include tungsten (Venturello, C.; Alneri, E.; Ricci, M. *J. Org. Chem.* 1983, 48, 3831; Venturello, C.; D'Aloisio, R. *J. Org. Chem.* 1988, 53, 1553; Ishii, Y.; Yamawaki, K.; Ura, T.; Yamada, H.; Yoshida, T.; Ogawa, M. *J. Org. Chem.* 1988, 53, 3587), manganese (Sato, K.; Aoki, M.; Ogawa, M.; Hashimoto, T.; Panyella, D.; Noyori, R. *Bull. Chem. Soc. Jpn.* 1997, 70, 905; Anelli, P. L.; Banfi, S.; Montanari, F.; Quici, S. *Chem. Commun.* 1989, 779; De Vos, D.; Bein, T. *Chem. Commun.* 1996, 917), and rhenium (De Vos, D. E.; Sels, B. F.; Reynaers, M.; Subba Rao, Y. V.; Jacobs, P. A. *Tetrahedron Lett.* 1998, 39, 3221; Sales, H. J.; Cesquini, R.; Mandelli, D.; Sato, S.; Schuchardt, U. *Stud. Surf Sci. Catal.* 2000, 130, 1661; Rudolph, J.; Reddy, K. L.; Chiang, J. P.; Sharpless, K. B. *J. Am. Chem. Soc.* 1997, 119, 6189) based systems, and also Brönsted acid catalysts such as formic acid. However, industrial application of these systems is not simple due to high catalyst costs and difficulties in separating the catalyst from the product. In addition, the acid catalysts promote hydrolysis of the epoxide to diols under the aqueous acid conditions. A possible solution to this would be the use of solid catalysts, with a lower tendency to cause hydrolysis. This approach would allow the design of continuous processes, in addition to the current batch reactions. Nevertheless, few solid catalysts are efficient in such reactions, i.e. Ti-silicalite (van Vliet, M. C. A.; Arends, I. W. C. E.; Sheldon, R. A. *Chem. Commun.* 1999, 821), vanadium containing silicates (Sheldon, R. A. in: Cornils, B.; Herrmann W. A. (Eds.), *Applied Homogeneous Catalysis with Organometallic Compounds*, VCH, Weinheim, 1997, 421), Ti-pillared clays (Yang, A.; Li, C.; Wang, S.; Lu, J.; Ying, P.; Xin, Q.; Shi, W. *Stud. Surf Sci. Catal.* 2000, 130, 221), hydrotalcites [(halfallah-Boudali, L.; Ghorbel, A.; Figueras, F.; Pinel, C. *Stud. Surf Sci. Catal.* 2000, 130, 1643; Fraile, J. M.; Garcia, J. I.; Marco, D.; Mayoral, J. A.; Sánchez, E.; Monzon, A.; Romeo, E. *Stud. Surf Sci. Catal.* 2000, 130, 1673), or some alumina catalysts, giving conversions to the epoxide not higher than 60% for alkyl chains, and generally requiring ethyl acetate as a solvent (Mandelli, D.; van Vliet, M. C. A.; Sheldon, R. A.; Schuchardt, U. *Appl. Catal. A: Gen.* 2001, 219, 209] or the use of anhydrous hydrogen peroxide (van Vliet, M. C. A.; Mandelli, D.; Arends, I. W. C. E.; Schuchardt, U.; Sheldon, R. *Green Chem.* 2001, 3, 243). However, all these solid catalyzed systems are still acidic, resulting in epoxide hydrolysis to diols.

Aqueous $H_2O_2$ is the most environmentally friendly and low-cost source of oxygen for these reactions, although it exhibits lower reactivity than the corresponding peracids. The reactive oxygen present in $H_2O_2$ is not highly selective but it could be easily converted to a selective peroxy species by an alumina-catalyzed reaction in the presence of a suitable organic acid. In this way, we would generate a peroxy carboxylic acid, more reactive than $H_2O_2$, to epoxidize unreactive substrates such as unsubstituted long-chain internal alkenes under solventless conditions. Additionally, basic alumina will be used to circumvent the hydrolysis of the epoxide acid-catalyzed product, opening the way for the use of basic solid catalysts for epoxidation reactions. The final system is a cascade catalytic cycle where the active oxygen atom passes from $H_2O_2$ to alumina and then to the fatty acid, to generate the selective reactive epoxidizing species for the otherwise unreactive unsubstituted long-linear internal alkene chain. The role of the fatty acid is not only to transfer the active oxygen atom to the alkene but also to homogenize the biphasic aqueous-alkene solution [S. E. Brandolín, J. A. Scilipoti, A. E. Andreatta, I. Magario, 2022, 10.1021/acs.jced.1c00917]. Besides, the fatty acid can be recovered (Mas-Ballesté, R.; Que, L. Jr. *J. Am. Chem. Soc.* 2007, 129, 15964; Klein, J. E. M. N.; Knizia, G.; Rzepa, H. S. *ChemistryOpen* 2019, 8, 1244). This three-phase heterogeneous epoxidation process is different and eco-friendly compared to conventional systems. The use of the amphoteric solid catalyst alumina, with both acidic and basic sites, opens the catalyst design for the epoxidation reaction, and we use here slightly basic alumina to accelerate hydrophobic peracid formation as well as minimize any potential acid catalyzed diol formation. Also, alumina is readily available and cost effective.

Accordingly, a need exists for a simple, more efficient, and cost-effective process of producing epoxide compounds.

In light of the above, it would be desirable to develop a clean and environmentally friendly process of producing epoxide compounds. Furthermore, it would be desirable to develop an efficient process which provides higher conversion rate and higher selectivity.

Therefore, it is an object of the invention is to provide a simple, more efficient and repeatable process of preparing epoxide compounds.

It is another object of the invention is to use safe and inexpensive starting materials.

It is still another object of the invention is to use low-cost catalyst, which can be recycled and reused.

It is also an object of the invention to avoid using organic solvents and corrosive acids during the preparation reaction.

It is a further object of the invention to provide higher conversion rate and higher selectivity of epoxide compounds.

These needs and other needs are met by the various aspects of the present disclosure.

SUMMARY OF THE INVENTION

Methods of making and using epoxide compounds and their industrial applications are provided.

In one embodiment, an epoxide compound is prepared in one-step.

In some embodiments, a process for preparing an epoxide, can include heating a mixture of a plurality of alkenes and a fatty acid at about 25° C. to about 100° C.; wherein a plurality of alkenes having following formula (I):

wherein R and R' are H or alkyl chains having 8 to 20 carbon atoms, adding an aluminum oxide catalyst to the reaction mixture; injecting hydrogen peroxide solution over a period of about 1 hour to about 48 hours into the reaction mixture; decanting the water from the reaction mixture; and collecting the epoxide.

In another embodiment, an epoxide compound is prepared in two-steps.

In other embodiments, a process for preparing an epoxide, can include heating a fatty acid at about 25° C. to about 100° C. in a tank; adding an aluminum oxide catalyst to the reaction mixture; injecting hydrogen peroxide solution over a period of about 1 h hour to about 48 hours into the reaction mixture; decanting the water from the reaction mixture; collecting a dry peroxy acid; heating the dry peroxy acid at about 50° C. in a tank; adding a plurality of alkenes over 3 hours to over 48 hours to the tank; and wherein a plurality of alkenes having following formula (I):

wherein R and R' are H or alkyl chains having 8 to 20 carbon atoms, and collecting the epoxide.

DETAILED DESCRIPTION OF THE INVENTION

I. Definitions

The following terms are intended to have the meanings presented therewith below and are useful in understanding the description and intended scope of the present invention.

As used in the specification and the appended claims, the singular forms "a," "an" and "the" include plural referents unless the context clearly dictates otherwise. Thus, for example, reference to "a composition," or "a step" includes mixtures of two or more such functional compositions, steps, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "effective amount" refers to an amount that is sufficient to achieve the desired result or to have an effect on an undesired condition.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

As used herein, the term "compound" refers to salts, complexes, isomers, stereoisomers, diastereoisomers, tautomers, and isotopes of the compound or any combination thereof.

As used herein, the term "alkyl" refers to a noncyclic straight chain or branched, unsaturated or saturated hydrocarbon such as those containing from 1 to 10 carbon atoms, typically 1 to 30 otherwise designated $C_1$-$C_{30}$ alkyl. Representative saturated straight chain alkyls include methyl, ethyl, n-propyl, n-butyl, n-pentyl, n-hexyl, n-heptyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Lubricants," as defined herein, are substances (usually a fluid under operating conditions) introduced between two moving surfaces so to reduce the friction and wear between them. Base oils used in industrial or motor oils are generally classified by the American Petroleum Institute as being mineral oils (Group I, II, and III) or synthetic oils (Group IV and V). See American Petroleum Institute (API) Publication Number 1509.

"Pour point," as defined herein, represents the lowest temperature at which a fluid will pour or flow. See, e.g., ASTM International Standard Test Methods D 5950-96, D 6892-03, and D 97.

"Cloud point," as defined herein, represents the temperature at which a fluid begins to phase separate due to crystal formation. See, e.g., ASTM Standard Test Methods D 5773-95, D 2500, D 5551.

"Centistoke," abbreviated "cSt," is a unit for kinematic viscosity of a fluid (e.g., a lubricant), wherein 1 centistoke equals 1 millimeter squared per second (1 cSt=1 mm$^2$/s). See, e.g., ASTM Standard Guide and Test Methods D 2270-04, D 445-06, D 6074, and D 2983.

With respect to describing molecules and/or molecular fragments herein, "$R_n$," where "n" is an index, refers to a hydrocarbon group, wherein the molecules and/or molecular fragments can be linear and/or branched.

As defined herein, "$C_n$," where "n" is an integer, describes a hydrocarbon molecule or fragment (e.g., an alkyl group) wherein "n" denotes the number of carbon atoms in the fragment or molecule.

The prefix "bio," as used herein, refers to an association with a renewable resource of biological origin, such as resource generally being exclusive of fossil fuels.

The term "internal olefin," as used herein, refers to an olefin (i.e., an alkene) having a non-terminal carbon-carbon double bond (C=C). This is in contrast to "α-olefins" which do bear a terminal carbon-carbon double bond.

The term "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are used in their inclusive, open-ended, and non-limiting sense.

The term "effective," as that term is used in the specification and/or claims, means adequate to accomplish a desired, expected, or intended result.

Finally, unless stated to the contrary, all percentages provided herein are percentages by weight.

Throughout this document, where publications are referenced, the disclosures of these publications in their entireties are hereby incorporated by reference in order to more fully describe the present invention.

II. Preparation of Epoxide Compounds in One Step

According to various aspects of the disclosure, the invention relates to processes for preparing epoxide compounds. In further aspects, the invention relates to using epoxide compounds and their industrial applications. In one embodiment, an epoxide compound is prepared in one-step.

It was unexpectedly and surprisingly discovered that an epoxide compound was synthesized via a simple, more efficient, cost-effective one-step process as given in Scheme 1. Alkene, aluminum oxide catalyst, hydrogen peroxide solution and fatty acid were reacted yielding an epoxide compound as shown in Scheme 1. The process was a clean and environmentally friendly. The process used safe and inexpensive starting materials. Organic solvents and corrosive acids were not used during the preparation reaction of epoxides. The process yields higher conversion rate (>98%) and higher selectivity (100%) of the epoxide compounds. The catalysts used in the reaction are low-cost and can be recycled and reused.

Scheme 1

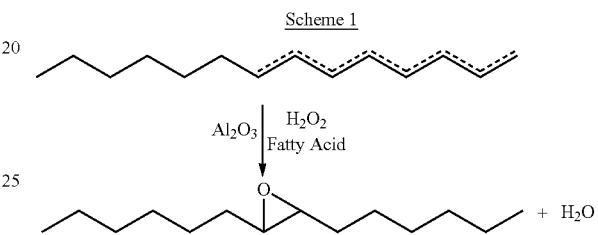

In some embodiments, a process for preparing an epoxide, can include heating a mixture of a plurality of alkenes and a fatty acid at about 25° C. to about 100° C.; wherein a plurality of alkenes having following formula (I):

R—CH=CH—R'  (I)

wherein R and R' are H or alkyl chains having 8 to 20 carbon atoms, adding an aluminum oxide catalyst to the reaction mixture; injecting hydrogen peroxide solution over a period of about 1 hour to about 48 hours into the reaction mixture; decanting the water from the reaction mixture; and collecting the epoxide.

In certain embodiments, the reaction time varies from about 1 hour to about 48 hours, preferably, the reaction time varies from about 7 hours to about 15 hours, and more preferably, the reaction time varies from about 0.5 hour to about 5 hours.

In further embodiments, the reaction temperature varies from about 25° C. to about 100° C., and preferably, the reaction temperature varies from about 50° C. to about 70° C.

In one embodiment, the alkenes are unsubstituted linear alkene chains.

In another embodiment, the alkenes have a double bond in any internal position of the alkene chains.

In some embodiments, the fatty acid having following formula (II):

R"—COOH  (II)

wherein R" are alkyl chains having 5 to 30 carbon atoms.

In further embodiments, the fatty acid can have 5 to 30 carbon atoms, and preferably, the fatty acid can have 8 to 18 carbon atoms.

In other embodiments, the amount of fatty acid varies from about 0.1 equivalent to about 2.0 equivalents, and preferably, the amount of fatty acid varies from about 0.2 equivalent to about 1.0 equivalents.

In one embodiment, the aluminum oxide is basic.

In some embodiments, the aluminum oxide can include powder, pellets, spheres or combinations thereof.

In other embodiments, the particle size of aluminum oxide powder varies from about 50 microns to about 500 microns.

In further embodiments, the particle size of aluminum oxide pellets varies from about 0.5 mm to about 5.0 mm.

In certain embodiments, the amount of aluminum oxide to alkenes varies from about 0.1 equivalent to about 2.0 equivalents, and preferably, the amount of aluminum oxide to alkenes varies from about 0.25 equivalent to about 1.0 equivalents.

In alternate embodiment, the aluminum oxide catalyst is recovered from the reaction and is reused. In one embodiment, the reuse of the alumina catalyst was performed. For example, the alumina catalyst can be quantitatively recovered after filtration, washed with a polar solvent (ethyl acetate, isopropanol) and dried using heat and/or vacuum. In other embodiment, the reuse of the alumina catalyst was performed inside the continuous reactor. For example, the alumina catalyst can be quantitatively recovered after heating from about 70° C. to about 150° C. for 7 hours under nitrogen flow.

In some embodiments, the concentration of hydrogen peroxide solution varies from about 30% to about 70%.

In one embodiment, the concentration of hydrogen peroxide solution is about 50%.

In other embodiments, the amount of hydrogen peroxide varies from about 1 equivalent to about 10 equivalents, and preferably, the amount of hydrogen peroxide varies from about 2 equivalents to about 6 equivalents.

In some embodiments, the process is carried out in the absence of a solvent or corrosive acids.

In other embodiments, the process is performed in a batch reactor.

In certain embodiments, the batch reactor has an agitation rate from about 200 rpm to about 1000 rpm.

In further embodiments, the process is performed in a continuous reactor.

In other embodiments, the continuous reactor has a flow rate from about 0.05 mL/h to about 1.0 mL/h.

In certain embodiments, a lubricant composition is prepared using an epoxide.

III. Preparation of Epoxide Compounds in Two Steps

In another embodiment, an epoxide compound was prepared in two-steps.

It was unexpectedly and surprisingly discovered that an epoxide compound was synthesized via a simple, more efficient, cost-effective two-step process as given in Scheme 2. Fatty acid was heated with hydrogen peroxide solution in the presence of aluminum oxide catalyst at about 25° C. to about 100° C. in a tank over a period of about 1 hour to about 48. The water was decanted from the reaction mixture and dry peroxy acid was collected. The dry peroxy acid was heated at about 50° C. in a tank, followed by an addition of an alkene over 3 hours to over 48 hours to the tank and collecting the epoxide compound as shown in Scheme 2.

Scheme 2

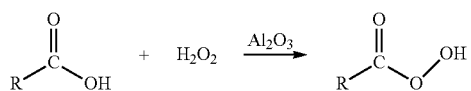

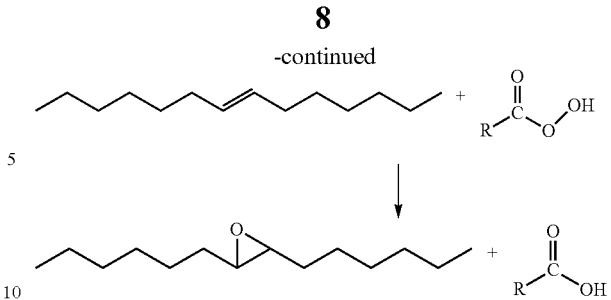

In other embodiments, a process for preparing an epoxide, can include heating a fatty acid at about 25° C. to about 100° C. in a tank; adding an aluminum oxide catalyst to the reaction mixture; injecting hydrogen peroxide solution over a period of about 1 hour to about 48 hours into the reaction mixture; decanting the water from the reaction mixture; collecting a dry peroxy acid; heating the dry peroxy acid at about 50° C. in a tank; adding a plurality of alkenes over 3 hours to over 48 hours to the tank; and wherein a plurality of alkenes having following formula (I):

R—CH=CH—R'  (I)

wherein R and R' are H or alkyl chains having 8 to 20 carbon atoms, and collecting the epoxide.

In some embodiments, the fatty acid having following formula (II):

R"—COOH  (II)

wherein R" are alkyl chains having 5 to 30 carbon atoms.

In further embodiments, the fatty acid can have 5 to 30 carbon atoms, and preferably, the fatty acid can have 8 to 18 carbon atoms.

In other embodiments, the amount of fatty acid varies from about 0.1 equivalent to about 2.0 equivalents, and preferably, the amount of fatty acid varies from about 0.2 equivalent to about 1.0 equivalents.

In one embodiment, the peroxy acid is generated in situ.

In other embodiments, the oxygen atom is transferred from hydrogen peroxide to the fatty acid generating peroxy acid.

In certain embodiments, the process carried out using the reactants as solvent.

In further embodiments, the fatty acid is recovered from the reaction and is reused.

In other embodiments, the fatty acid is recovered from the reaction mixture after reaction, filtration of the alumina and washings, and precipitation with basic water or extraction with organic solvent and water, and can be reused in a second run.

IV. Industrial Applications

It was unexpectedly and surprisingly discovered that an epoxide compound was synthesized in one-step and two-step processes. The process is a clean and environmentally friendly. The process uses safe and inexpensive starting materials. Organic solvents and corrosive acids are not used during the preparation reaction of epoxides. The process yields higher conversion rate (>98%) and higher selectivity (100%) of the epoxide compounds. The catalysts used in the reaction are low-cost and can be recycled and reused. Industrial applications of epoxide compounds include, but not limited to, lubricants, personal care products, paints, coatings, plastics, and plasticizers. Epoxides can also be used as stabilizers and acid scavenger additives, or can be used as intermediates to form esters, bio-resins or cross linkers for polymer synthesis.

EXAMPLES

To provide a better understanding of the foregoing discussion, the following non-limiting examples are provided. Although the examples may be directed to specific embodiments, they are not to be viewed as limiting the invention in any specific respect.

Example 1: Preparation of Epoxide Via Batch Reactor Process

Batch reaction procedure. The corresponding amounts of $Al_2O_3$ catalyst (25 to 50 wt %), alkene (5 mmol), and fatty acid (0.25 eq) were placed in a 10 mL round bottom flask equipped with a magnetic stirrer at 70° C. $H_2O_2$ between 35 and 50% (2-6 eq) was then added in one pot, and stirred for the required time. After that, the vial was cooled to separate the phases (solid, organic and aqueous), and the mixture was analyzed by GC after dilution in ethyl acetate. The product was isolated by filtration to eliminate the alumina and then by extraction of the organic phase. Alkene conversion to epoxide was measured to be 98% with >99% selectivity.

Example 2: Alumina Reuse Reaction Procedure

The alumina catalyst was recovered after filtration, washed with ethyl acetate 3 times and dried in vacuum overnight. After that, the corresponding amounts of $Al_2O_3$ catalyst (25 to 50 wt %), alkene (5 mmol), and acid (0.25 eq) were placed in a 10 mL round bottom flask equipped with a magnetic stirrer at 70° C. $H_2O_2$ between 35 and 50% (2-6 eq) was then added in one pot, and stirred for the required time. After that, the vial was cooled to separate the phases (solid, organic and aqueous), and the mixture was analyzed by GC after dilution in ethyl acetate. The product was isolated by filtration to eliminate the alumina and then by extraction of the organic phase. The alumina reuse procedure was repeated 3 times. Alkene conversion to epoxide in each case was measured to be 97-99% with >99% selectivity.

Example 3: Preparation of Epoxide Via Continuous Reactor Process

Reaction procedure for continuous reactor. $Al_2O_3$ in 1/16" spheres were placed inside a tubular reactor and heated at 70° C. A stirred liquid mixture 4:6 of alkene with 0.25 eq. of acid and $H_2O_2$ 30-50 wt % was passed over the fixed bed of alumina at a velocity oscillating between 0.25 ml/h and 2.0 ml/h. At 1.0 ml/h flow rate, alkene conversion to epoxide was measured to be 25-30% per pass with >99% selectivity. After multiple passes, >80% conversion can be achieved.

While in the foregoing specification this invention has been described in relation to certain embodiments thereof, and many details have been put forth for the purpose of illustration, it will be apparent to those skilled in the art that the invention includes additional embodiments and that certain of the details described herein can be varied considerably without departing from the basic principles of the invention. Although we have described the preferred embodiments for implementing our invention, it will be understood by those skilled in the art to which this disclosure is directed that modifications and additions may be made to our invention without departing from its scope.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A process for preparing an epoxide, comprising:
   heating a mixture of a plurality of alkenes and a fatty acid at about 25° C. to about 100° C.;
   wherein a plurality of alkenes having following formula (I):

R—CH═CH—R'  (I)

wherein R and R' are H or alkyl chains having 8 to 20 carbon atoms,
   adding an aluminum oxide catalyst to the reaction mixture;
   injecting hydrogen peroxide solution over a period of about 1 hour to about 48 hours into the reaction mixture;
   decanting the water from the reaction mixture; and
   collecting the epoxide.

2. The process of claim 1, wherein the alkenes are unsubstituted linear alkene chains and the alkenes have a double bond in any internal position of the alkene chains.

3. A process for preparing an epoxide, comprising:
   heating a mixture of a plurality of alkenes and a fatty acid at about 25° C. to about 100° C.;
   wherein a plurality of alkenes having following formula (I):

R—CH═CH—R'  (I)

wherein R and R' are H or alkyl chains having 8 to 20 carbon atoms,
   wherein the fatty acid having following formula (II):

R"—COOH  (II)

wherein R" are alkyl chains having 5 to 30 carbon atoms
   adding an aluminum oxide catalyst to the reaction mixture;
   injecting hydrogen peroxide solution over a period of about 1 hour to about 48 hours into the reaction mixture;
   decanting the water from the reaction mixture; and
   collecting the epoxide.

4. The process of claim 1, wherein the amount of fatty acid varies from about 0.1 equivalent to about 2.0 equivalents.

5. The process of claim 1, wherein the aluminum oxide is basic and the aluminum oxide comprises powder, pellets, spheres or combinations thereof.

6. The process of claim 5, wherein the particle size of aluminum oxide powder varies from about 50 microns to about 500 microns.

7. The process of claim 5, wherein the particle size of aluminum oxide pellets varies from about 0.5 mm to about 5.0 mm.

8. The process of claim 1, wherein the amount of aluminum oxide to alkenes varies from about 0.1 equivalent to about 2.0 equivalents.

9. The process of claim 1, wherein the aluminum oxide catalyst and the fatty acid are recovered from the reaction and is reused.

10. The process of claim 1, wherein the concentration of hydrogen peroxide solution varies from about 30% to about 70%.

11. The process of claim 1, wherein the amount of hydrogen peroxide varies from about 1 equivalent to about 10 equivalents.

12. The process of claim 1, wherein the process is carried out in the absence of a solvent or corrosive acids.

13. The process of claim 1, wherein the process is performed in a batch reactor, continuous reactor or combinations thereof.

14. The process of claim 13, wherein the batch reactor has an agitation rate from about 200 rpm to about 1000 rpm.

15. The process of claim 13, wherein the continuous reactor has a flow rate from about 0.05 mL/h to about 1.0 mL/h.

16. A process for preparing an epoxide, comprising:
heating a fatty acid at about 25° C. to about 100° C. in a tank;
adding an aluminum oxide catalyst to the reaction mixture;
injecting hydrogen peroxide solution over a period of about 1 h hour to about 48 hours into the reaction mixture;
decanting the water from the reaction mixture;
collecting a dry peroxy acid;
heating the dry peroxy acid at about 50° C. in a tank;
adding a plurality of alkenes over 3 hours to over 48 hours to the tank; and
wherein a plurality of alkenes having following formula (I):

R—CH═CH—R'  (I)

wherein R and R' are H or alkyl chains having 8 to 20 carbon atoms, collecting the epoxide.

17. A process for preparing an epoxide, comprising:
heating a fatty acid at about 25° C. to about 100° C. in a tank;
wherein the fatty acid having following formula (II):

R''—COOH  (II)

wherein R'' are alkyl chains having 5 to 30 carbon atoms
adding an aluminum oxide catalyst to the reaction mixture;
injecting hydrogen peroxide solution over a period of about 1 h hour to about 48 hours into the reaction mixture;
decanting the water from the reaction mixture;
collecting a dry peroxy acid;
heating the dry peroxy acid at about 50° C. in a tank;
adding a plurality of alkenes over 3 hours to over 48 hours to the tank; and
wherein a plurality of alkenes having following formula (I):

R—CH═CH—R'  (I)

wherein R and R' are H or alkyl chains having 8 to 20 carbon atoms, collecting the epoxide.

18. A process for preparing an epoxide, comprising:
heating a fatty acid at about 25° C. to about 100° C. in a tank;
adding an aluminum oxide catalyst to the reaction mixture;
injecting hydrogen peroxide solution over a period of about 1 h hour to about 48 hours into the reaction mixture;
decanting the water from the reaction mixture;
collecting a dry peroxy acid;
heating the dry peroxy acid at about 50° C. in a tank;
adding a plurality of alkenes over 3 hours to over 48 hours to the tank; and
wherein a plurality of alkenes having following formula (I):

R—CH═CH—R'  (I)

wherein R and R' are H or alkyl chains having 8 to 20 carbon atoms, collecting the epoxide,
wherein the peroxy acid is generated in situ and the oxygen atom is transferred from hydrogen peroxide to the fatty acid generating peroxy acid.

19. A process for preparing an epoxide, comprising:
heating a mixture of a plurality of alkenes and a fatty acid at about 25° C. to about 100° C.;
wherein a plurality of alkenes having following formula (I):

R—CH═CH—R'  (I)

wherein R and R' are H or alkyl chains having 8 to 20 carbon atoms,
adding an aluminum oxide catalyst to the reaction mixture;
injecting hydrogen peroxide solution over a period of about 1 hour to about 48 hours into the reaction mixture;
decanting the water from the reaction mixture; and
collecting the epoxide,
wherein the process carried out using the reactants as solvent.

20. The process of claim 1, wherein the conversion rate is >98% and selectivity of the epoxide is 100%.

* * * * *